(12) United States Patent
Schulze et al.

(10) Patent No.: US 6,589,255 B2
(45) Date of Patent: Jul. 8, 2003

(54) VESSEL EVERSION INSTRUMENT WITH FILAMENT ELEMENTS

(75) Inventors: Dale R. Schulze, Lebanon, OH (US); Michael F. Clem, Maineville, OH (US)

(73) Assignee: Ethicon, Inc., Somerville, NJ (US)

( * ) Notice: Subject to any disclaimer, the term of this patent is extended or adjusted under 35 U.S.C. 154(b) by 156 days.

(21) Appl. No.: 09/894,316

(22) Filed: Jun. 28, 2001

(65) Prior Publication Data

US 2003/0004524 A1 Jan. 2, 2003

(51) Int. Cl.[7] .............................................. A61B 17/04
(52) U.S. Cl. ...................................................... 606/149
(58) Field of Search ........................................ 606/149

(56) References Cited

U.S. PATENT DOCUMENTS

| | | |
|---|---|---|
| 2,086,371 A | 7/1937 | Tear |
| 2,940,452 A | 6/1960 | Smialowski |
| 3,040,748 A | 6/1962 | Klein et al. |
| 3,057,355 A | 10/1962 | Smialowski et al. |
| 3,180,337 A | 4/1965 | Smialowski |
| 3,908,662 A | 9/1975 | Razgulov et al. |
| 4,470,415 A | 9/1984 | Wozniak |
| 4,622,970 A | 11/1986 | Wozniak |
| 2002/0198545 A1 * | 12/2002 | Hess et al. ................ 606/149 |

* cited by examiner

*Primary Examiner*—Rodney M. Lindsey
(74) *Attorney, Agent, or Firm*—Emil Skula

(57) ABSTRACT

An instrument is provided for everting an end of a vessel over an end of a tubular workpiece. The instrument comprises a body having an axial bore, a piston slideably contained inside of the axial bore, and a plunger coaxially mounted within the axial bore and axially movable between an extended position and a retracted position. The instrument further comprises a spring mounted within the axial bore and biasing the plunger and the piston to separate. The instrument further comprises a plurality of filaments, each filament having a distal end attached to the plunger and a proximal end attached to the piston, and each of the filaments tensioned by the spring. The instrument further comprises a plurality of guides circumferentially spaced apart in the distal end of the body, each guide supporting one of the filaments radially apart from the plunger, the plunger and the filaments insertable into the lumen of the vessel when the plunger is in the extended position.

20 Claims, 3 Drawing Sheets

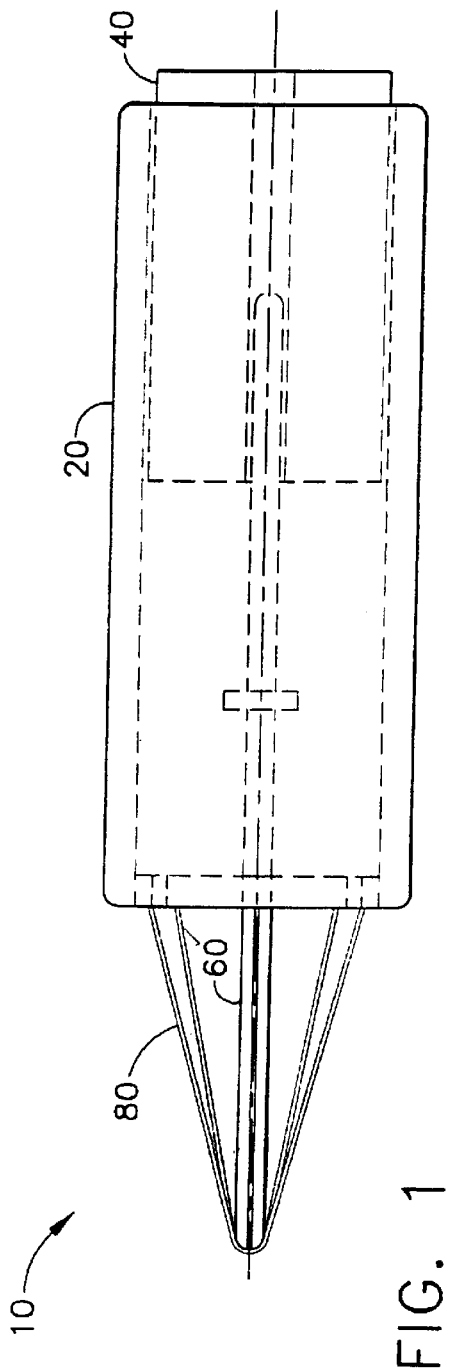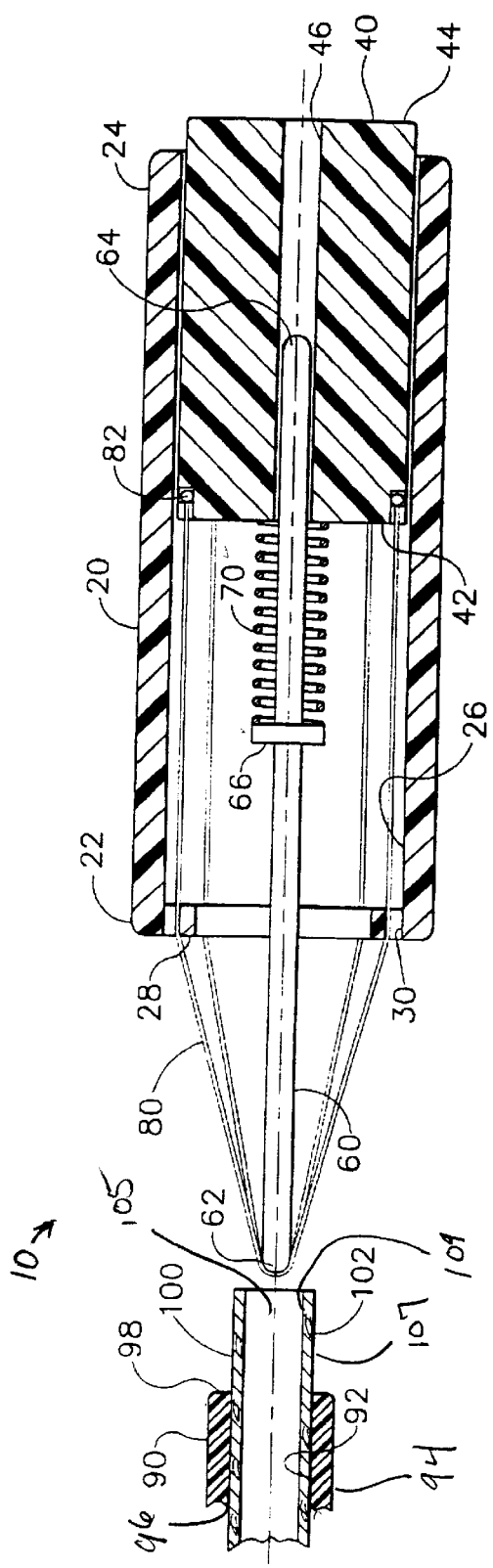

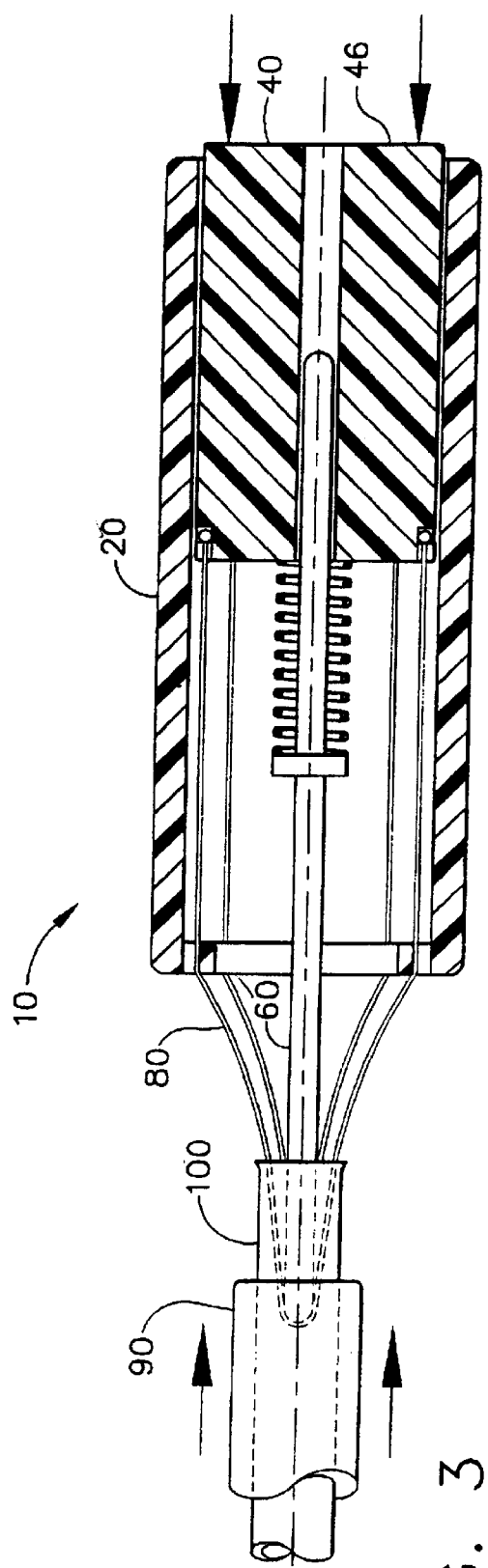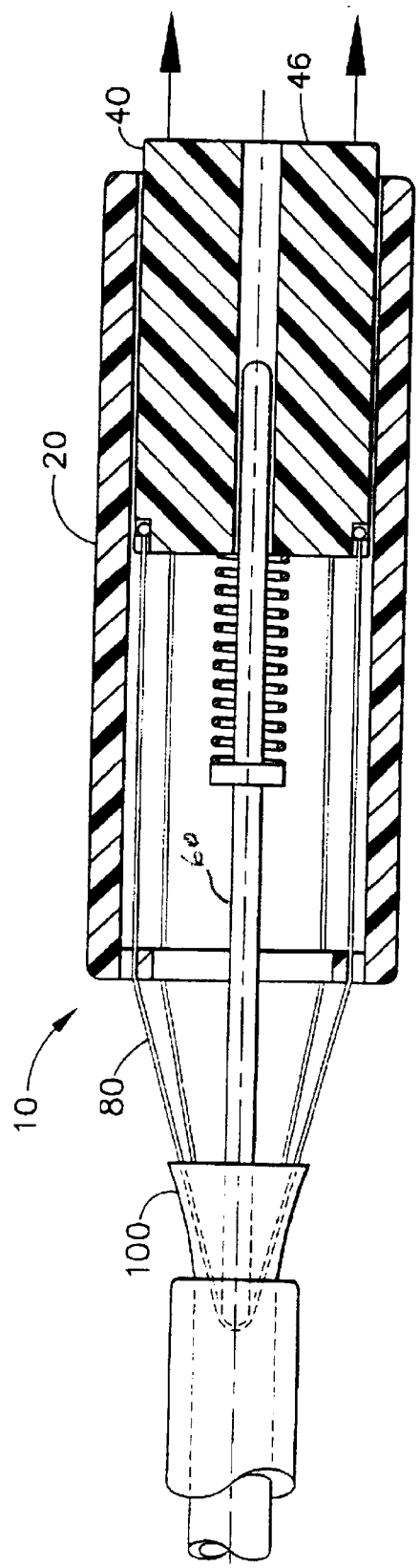

VESSEL EVERSION INSTRUMENT WITH FILAMENT ELEMENTS

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomosis surgical procedures are common in the field of cardiac surgery. These procedures are conventionally used for repairing a damaged or diseased blood vessel. In a typical anastomosis procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (e.g., under 0.001 inch diameter) to suture the vessels together. The vessels may be joined conventionally as end-to-end, end-to-side, or side-to-side anastomoses. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as, for example, a segment of saphenous vein harvested from the patient) to a side of a target vessel (e.g., the stenosed coronary artery). For a proximal anastomosis in a conventional CABG procedure, the surgeon sutures a proximal end of the graft vessel to the side of the aorta.

As this field of art has progressed, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel, when the opposite end is already attached to the patient (e.g., at the distal anastomosis of a patient undergoing a CABG procedure). The eversion device should also allow for the proper length of everted tissue over the tube, bushing, or the like, depending on the requirements of the anastomosis device/method to be used. Finally, it is desirable that the eversion device be low cost and yet operate reliably.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices which engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel. Accordingly, an eversion instrument for everting an end of a vessel is disclosed. The instrument has a tubular body member having an axial bore, a distal end and a proximal end. The proximal end has an opening in communication with the axial bore and the distal end has an opening in communication with the axial bore. A piston is slideably contained within the axial bore. The piston has a distal end, a proximal end, and an axial passage. There is a plunger rod member having a distal end and a proximal end. At least a proximal section of the rod member is slideably mounted within the axial passage of the piston and is axially movable between an extended position and a retracted position. A distal end section of the plunger rod extends distally out through the distal opening of the tubular body member. A spring is mounted to the rod member for biasing the plunger with respect to and the piston. The instrument has a plurality of flexible filaments. Each filament has a distal end attached to the distal end of the plunger rod and a proximal end attached to the piston. Each of the filaments is tensioned by the spring biasing the plunger rod with respect to the piston. A plurality of guides circumferentially spaced apart are located at the distal end of the tubular body member. Each guide has a passage for receiving and supporting one or more of the filaments radially apart from the plunger rod. In operation, a distal end section of the plunger and distal end sections of the filaments are insertable into a lumen of a vessel when the plunger rod is in the extended position to evert the end of a vessel.

Another aspect of the present invention is a method of everting the end of a vessel. An eversion instrument is provided. The instrument has a tubular body member having an axial bore, a distal end and a proximal end. The proximal end has an opening in communication with the axial bore and the distal end has an opening in communication with the axial bore. A piston is slideably contained within the axial bore. The piston has a distal end, a proximal end, and an axial passage. There is a plunger rod member having a distal end and a proximal end. At least a proximal section of the rod member is slideably mounted within the axial passage of the piston and is axially movable between an extended position and a retracted position. A distal end section of the plunger rod extends distally out through the distal opening of the tubular body member. A spring is mounted to the rod member for biasing the plunger with respect to and the piston. The instrument has a plurality of flexible filaments. Each filament has a distal end attached to the distal end of the plunger rod and a proximal end attached to the piston. Each of the filaments is tensioned by the spring biasing the plunger rod with respect to the piston. A plurality of guides circumferentially spaced apart are located at the distal end of the tubular body member. Each guide has a passage for receiving and supporting one or more of the filaments radially apart from the plunger rod. A distal end section of the plunger and distal end sections of the filaments are insertable into a lumen of a vessel when the plunger rod is in the extended position. A tubular workpiece is provided. The tubular workpiece has a tubular member having an axial passage, a distal opening and a proximal opening both of which communicate with the axial passage. The tubular member also has an outer surface, a proximal end, and a distal end. Next, a vessel having a lumen is inserted into the axial passage of the tubular member such that an end section of the vessel extends out from the distal end of the tubular member. The distal end section of the plunger and the distal end sections of the filaments are inserted into the lumen of the vessel. The end section of the vessel is then invaginated over the distal end of the distal end of the tubular member onto its outer surface. Then, the end section of the plunger and the distal end sections of the filaments are withdrawn from the lumen of the end section of the vessel. The eversion is completed by withdrawing the everted vessel out from the tubular member.

Yet another aspect of the present invention is the combination of the above-described eversion instrument of the present invention and a tubular workpiece.

These and other aspects and advantages of the present invention will become more apparent from the following description and accompanying drawings.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 1 is a side view of an eversion instrument 10 of the present invention;

FIG. 2 is a cross-sectional view of the eversion instrument 10 of FIG. 1, shown in proximity to a vessel 100 held in a tube 90;

FIG. 3 is a cross-sectional view of the eversion instrument 10 of FIG. 1, depicting a step of inserting eversion instrument 10 into a vessel 100;

FIG. 4 is a cross-sectional view of the eversion instrument 10 of FIG. 1, depicting a step of flaring a vessel portion 102 with eversion instrument 10;

DETAILED DESCRIPTION OF THE INVENTION

Figure 5:
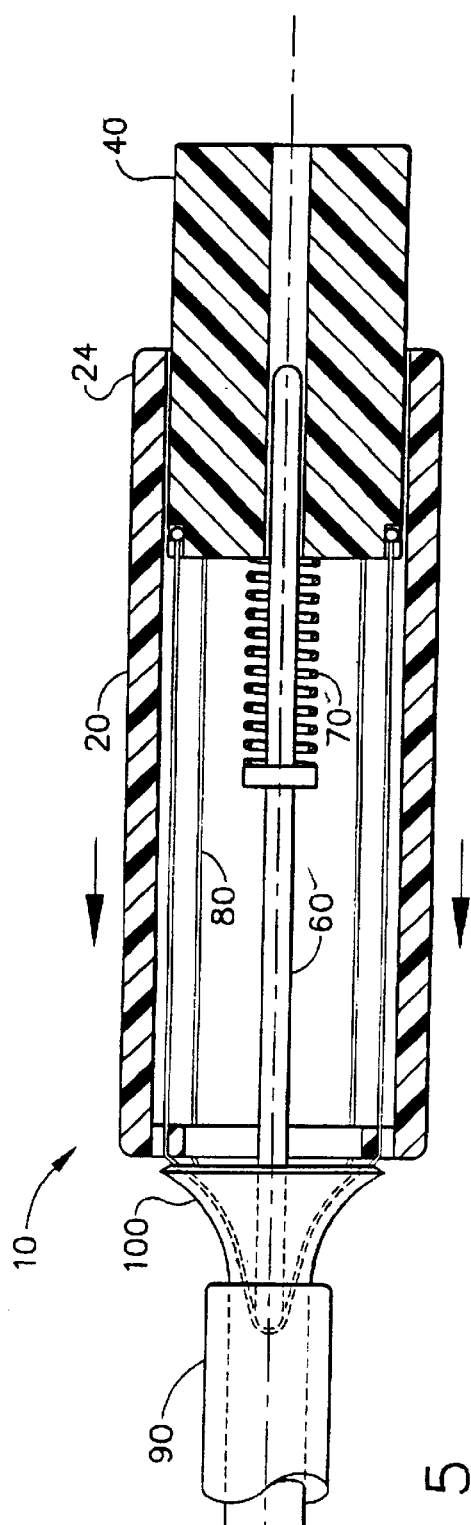
FIG. 5 is a cross-sectional view of the eversion instrument 10 of FIG. 1, depicting a step of invaginating vessel portion 102 with eversion instrument 10.

FIG. 1 illustrates a preferred embodiment of an eversion instrument 10 of the present invention. The instrument 10 is used for everting a vessel end section 102 (see FIG. 2) of a vessel 100 over the end of a tube 90, also referred to as a tubular workpiece 90. Vessel 100 may be a blood vessel, such as a segment of the greater saphenous vein, having a diameter of about 2–8 mm, although other hollow organs having approximately the same size may be everted using eversion instrument 10. Tube 90 holds vessel 100 and is representative of numerous kinds of bushings, ferrules, tubes, and specialized devices having an approximately cylindrical shape with an axial bore through it. The tube 90 is seen to have interior surface 96 and exterior surface 94. Vessel 100 inserts into an axial bore or lumen 92 of tube 90 so that a vessel section 102 of vessel 100 extends beyond a tube end 98 of tube 90. The vessel 100 is seen to have lumen 105, interior surface 109 and exterior surface 107. The length of vessel section 102 of vessel 100 depends primarily on the desired length of eversion, but is approximately in the range of 5–15 mm. The operator of eversion instrument 10, an assistant, or a mechanical holding device holds tube 90 as the operator uses eversion instrument 10 to evert vessel section 102 onto tube 90.

As shown in FIG. 1, eversion instrument 10 comprises a cylinder 20 containing a piston 40, a mandrel 60 coaxially mounted to piston 40 and extending from cylinder 20, and a plurality of flexible filaments 80 attached to mandrel 60 and passing into cylinder 20. Piston 40, cylinder 20, and mandrel 60 are preferably made of a rigid plastic suitable for contact with vessel 100, although other biocompatible materials may be used including surgical grade stainless steel, glass, etc. Filaments 80 are preferably made from any sterile, non-metallic materials currently used for surgical sutures, including polyester braided suture, polypropylene suture, and catgut. Although, if desired, but not preferred, filaments 80 may be constructed from flexible biocompatible metals. The number of filaments may vary, and is sufficient to provide effective eversion, and is preferably in the range of 8–12 filaments. FIG. 2 is a cross-sectional side view of eversion instrument 10 shown in alignment for insertion into lumen 105 of vessel 100, which is shown held in lumen 92 of tube 90. Cylinder 20 includes a distal end 22, a proximal end 24, and an axial bore 26. Piston 40 includes a distal end 42, a proximal end 44, and an axial bore 46. Piston 40 inserts slideably into axial bore 26 of cylinder 20. Mandrel 60 is an elongated, rigid rod or tube having a distal end 62, a proximal end 64, and a ring 66 attached approximately halfway between distal end 62 and proximal end 64. Proximal end 64 of mandrel 60 inserts slideably into axial bore 46 of piston 40. A spring 70, preferably a coiled, stainless steel wire, compression spring, mounts loosely over mandrel 60 between ring 66 and distal end 42 of piston 40, providing a light, biasing force to mandrel 60 in the distal (left, as shown in FIG. 2) direction. Each one of filaments 80 attaches to distal tip 62 of mandrel 60. Cylinder 20 includes a flange 28 on distal end 22 and projecting into axial bore 26. Flange 28 includes a plurality of guide holes 30. Each one of filaments 80 passes through one of guide holes 30, and attaches at one of a plurality of terminations on distal end 42 of piston 40. As shown in FIG. 2, filaments 80 transcribe a conical array about the longitudinal axis of cylinder 20 and extend from distal end 22 of cylinder 20. Tension in each of filaments 80 is maintained by the biasing force provided by spring 70.

Figure 6:
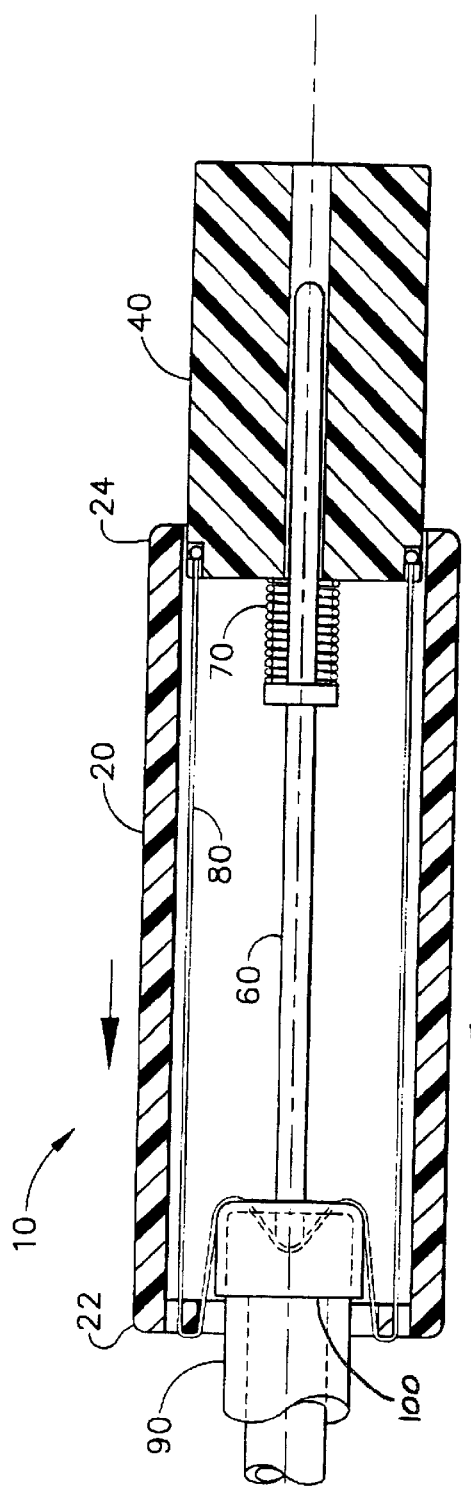
FIG. 6 is a sectional view of the eversion instrument 10 of FIG. 1, depicting a step of everting vessel portion 102 over the end of tube 90.

FIGS. 3–6 depict the steps of the operational sequence for using eversion instrument 10. Referring initially to FIG. 3, there is illustrated a first step of inserting mandrel 60 into lumen 105 of vessel 100, which is held in tube 90. The operator holds cylinder 20 between the thumb and second finger, while pressing lightly on proximal end 46 of piston 40 with the index finger in order to slacken filaments 80 during insertion. FIG. 4 shows eversion instrument 10 being used in a second step of flaring end section 102 of vessel 100. The operator removes pressure applied to distal end 46 of piston 40 while still holding cylinder 20 so that filaments 80 tension into the conical array about mandrel 60. FIG. 5 shows eversion instrument 10 being used in a third step of invaginating end 102 of vessel 100. The operator moves cylinder 20 in the distal (left) direction, allowing piston 40 to extend out of the proximal end 24 of cylinder 20. Mandrel 60 retracts out of vessel 100 slightly. Filaments 80 remain lightly tensioned due to the biasing force provided by spring 70. Maintaining this tension helps to flare and invaginate end section 102 of vessel 100, thus facilitating the eversion of end section 102 of vessel 100 over end 98 of tube 90. FIG. 6 shows eversion instrument 10 being used in a fourth step of completing the eversion of end section 105 of vessel 100 over tube 90 by moving distal end 22 of cylinder 20 over tube 90, so that filaments 80 pull end section 105 of vessel 100 over end 98 of tube 90, and further such that exterior surface 107 of vessel 100 is in contact with or proximate exterior surface 94 of end section 98. Mandrel 60 retracts almost completely out of vessel 100, compressing spring 70 and extending piston 40 further out proximal end 24 of cylinder 20. Filaments 80 remain tensioned, facilitating the completion of the eversion end section 105 of vessel 100 onto tube 90. In a final fifth step (not shown), the operator moves eversion instrument 10 apart from vessel 100, pushing piston 40 back into cylinder 20 and allowing mandrel 60 to extend from proximal end 22 of cylinder 20. Steps 15 may be repeated as often as necessary to achieve the desired eversion of vessel 100 onto tube 90.

Eversion instrument 10 as described for the specific embodiment shown in FIGS. 1–6 is constructed of low cost materials and preferably is supplied to the end user as a sterilized unit intended for single patient use. Re-sterilizable embodiments of eversion instrument 10 intended for multi-patient use will become apparent to those skilled in the art. The following example is illustrative of the principles and practice of the present invention, although not limited thereto.

EXAMPLE

A patient undergoing cardiac coronary artery bypass graft (CABG) surgery is prepared for surgery and anesthetized in a conventional manner in accordance with the prevailing medical standards. The patient's chest is opened in a conventional manner by cutting through the sternum and expanding the rib cage with a conventional surgical retractor instrument. The patient's heart is accessed in a conventional manner and the patient is connected to a pulmonary bypass machine and the heart is stopped. A section of the patient's saphenous vein, which has already been harvested by this time, is prepared for use as a graft vessel. The graft vessel end that is to be attached to the aorta for the proximal anastomosis is everted using an eversion instrument of the present invention as already described in the detailed description and shown in FIGS. 2–6. In FIG. 6, vessel 100 is shown everted over tube 90. One embodiment of tube 90 is disclosed in published patent application WO0056228, "Low Profile Anastomosis Connector", filed on Mar. 20, 2000, assigned to By-Pass, Inc., and which is hereby incorporated herein by reference. As described in WO0056228, a metallic anastomosis connector comprising a plurality of ring segments is used to fasten the graft vessel to another vessel such as the aorta. The distal end of the graft vessel is then be anastomotically attached to a coronary artery on the heart using a conventional hand suturing method. Additional bypasses are performed in the same manner or variations, depending on the patient's condition and anatomy. The remainder of the CABG procedure is conducted in a conventional manner and includes the steps of inspecting and repairing the grafts for leaks, checking blood flow, removing the patient from the pulmonary bypass machine, and closing the surgical incision.

The eversion instruments and eversion methods of the present invention have many advantages. The present invention is less traumatic to the intima of the vessel during the eversion procedure than conventional surgical graspers and the like. The present invention is easy for the surgeon to use without assistance and requires only a few steps to operate. The present invention is useful for a wide range of blood vessel sizes, particularly small vessels, e.g., having a diameter of about 2–3 mm or less. In addition, the present invention is useful on one end of a vessel, when the opposite end is already attached to the patient (e.g., at the distal anastomosis of a patient undergoing a CABG procedure). The present invention also allows for the proper length of everted tissue over the tube, bushing, or the like, depending on the requirements of the anastomosis device or method being used. Finally, the present invention may be manufactured inexpensively.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

Although this invention has been shown and described with respect to detailed embodiments thereof, it will be understood by those skilled in the art that various changes in form and detail thereof may be made without departing from the spirit and scope of the claimed invention.

What is claimed is:

1. An instrument for everting an end of a vessel, comprising:

a tubular body member having an axial bore, a distal end and a proximal end, wherein said proximal end has an opening in communication with the axial bore and wherein the distal end has an opening in communication with the axial bore;

a piston movable within the axial bore, the piston having a distal end, a proximal end, and an axial passage;

a plunger rod having a distal end and a proximal end, wherein at least a proximal section of the plunger rod is slideably mounted within the axial passage and axially movable between an extended position, wherein a distal end section of the plunger rod extends distally out through the distal opening of the tubular body member, and a retracted position;

a spring disposed between said plunger rod and said piston for biasing the plunger rod with respect to the piston;

a plurality of flexible filaments, each filament having a distal end attached to the distal end of the plunger rod and a proximal end attached to the piston.

2. The instrument of claim 1, wherein the tubular body member is transparent.

3. The instrument of claim 1, wherein the plurality of guides comprises a plurality of apertures formed into the distal end of the tubular body member and in communication with the axial bore.

4. The instrument of claim 1, wherein the spring comprises a coil spring having a distal end and a proximal end.

5. The instrument of claim 4, wherein then spring is coaxially mounted over the plunger rod.

6. The instrument of claim 5, wherein the plunger rod additionally comprises a collar member mounted thereto having a proximal end face and a distal end face, and wherein the distal end of the spring engages the proximal end face and wherein the proximal end of the spring engages the distal end of the piston.

7. The instrument of claim 1, wherein the tubular body member further comprises a flange member mounted to the distal end and having an opening therethrough in communication with the distal opening.

8. The combination comprising:
I. a tubular member having a proximal end, a distal end, an axial passage, an interior surface, and an exterior surface; and,
II. an instrument for everting the end of a vessel over the end of a tubular member, comprising:
  a tubular body member having an axial bore, a distal end and a proximal end, wherein said proximal end has an opening in communication with the axial bore and wherein the distal end has an opening in communication with the axial bore;
  a piston movable within the axial bore, the piston having a distal end, a proximal end, and an axial passage;
  a plunger rod having a distal end and a proximal end, wherein at least a proximal section of the plunger rod is slideably mounted within the axial passage and axially movable between an extended position, wherein a distal end section of the plunger rod extends distally out through the distal opening of the tubular body member, and a retracted position;
  a spring disposed between said plunger rod and said piston for biasing the plunger rod with respect to the piston;
  a plurality of flexible filaments, each filament having a distal end attached to the distal end of the plunger rod and a proximal end attached to the piston, wherein each of said filaments is tensioned by said spring biasing the plunger rod with respect to the piston; and,
  a plurality of guides circumferentially spaced apart in the distal end of the tubular body member, each guide having a passage for receiving and supporting one of said filaments radially apart from the plunger rod,
  wherein a distal end section of the plunger and distal end sections of the filaments are insertable into a lumen of a vessel when the plunger rod is in the extended position.

9. The combination of claim 8, wherein the tubular body member is transparent.

10. The combination of claim 8, wherein the plurality of guides comprises a plurality of apertures formed into the distal end of the tubular body member and in communication with the axial bore.

11. The combination of claim 8, wherein the spring comprises a coil spring having a distal end and a proximal end.

12. The combination of claim 11, wherein then spring is coaxially mounted over the plunger rod.

13. The combination of claim 12, wherein the plunger rod additionally comprises a collar member mounted thereto having a proximal end face and a distal end face, and wherein the distal end of the spring engages the proximal end face and wherein the proximal end of the spring engages the distal end of the piston.

14. The combination of claim 8, wherein the tubular body member further comprises a flange member mounted to the distal end and having an opening therethrough in communication with the distal opening.

15. A method for everting the end of a vessel over an end of a tubular workpiece comprising the step of:
  providing an instrument comprising
    a tubular body member having an axial bore, a distal end and a proximal end, wherein said proximal end has an opening in communication with the axial bore and wherein the distal end has an opening in communication with the axial bore;
    a piston movable within the axial bore, the piston having a distal end, a proximal end, and an axial passage;
    a plunger rod having a distal end and a proximal end, wherein at least a proximal section of the plunger rod is slideably mounted within the axial passage and axially movable between an extended position, wherein a distal end section of the plunger rod extends distally out through the distal opening of the tubular body member, and a retracted position;
    a spring disposed between said plunger rod and the piston for biasing the plunger rod with respect to the piston;
    a plurality of flexible filaments, each filament having a distal end attached to the distal end of the plunger rod and a proximal end attached to the piston, wherein each of said filaments is tensioned by said spring biasing the plunger rod with respect to the piston;
  providing a tubular workpiece comprising a tubular member having an axial passage, a distal opening and a proximal opening both in communication with the axial passage, an outer surface, a proximal end, and a distal end;
  inserting the vessel into the axial passage of the tubular member such that an end section of the vessel extends out from the distal end of the tubular member;
  inserting the distal end section of the plunger and the distal end sections of the filaments into the lumen of the vessel;
  invaginating the end of the vessel over the distal end of the distal end of the tubular member onto its outer surface; and,
  withdrawing the end section of the plunger and the distal end sections of the filaments from the lumen of the end of the vessel.

16. The method of claim 15, additionally comprising the step of moving the tubular body member in a distal direction such that at least a section of the distal end of the tubular member moves over the distal end of the tubular member such that the distal end of the tubular member is contained within the axial bore of the tubular body member.

17. The method of claim 15 additionally comprising the step of removing the vessel from the tubular member.

18. The instrument of claim 1, wherein each of the filaments is tensioned by the spring.

19. The instrument of claim 1, comprising a plurality of guides circumferentially spaced apart in the distal end of the tubular body member, each guide having a passage for receiving and supporting one of the filaments radially apart from the plunger rod.

20. The instrument of claim 1, wherein the distal end section of the plunger rod is insertable into a lumen of a vessel when the plunger rod is in the extended position.

* * * * *